United States Patent [19]
Williams et al.

[11] Patent Number: 5,485,494
[45] Date of Patent: Jan. 16, 1996

[54] MODULATION OF X-RAY TUBE CURRENT DURING CT SCANNING

[75] Inventors: Kenneth R. Williams, Muskego; Herbert K. Koehl, Milwaukee; Jonathan R. Schmidt, Wales, all of Wis.

[73] Assignee: General Electric Company, Milwaukee, Wis.

[21] Appl. No.: 285,253

[22] Filed: Aug. 3, 1994

[51] Int. Cl.⁶ ........................................... A61B 6/00
[52] U.S. Cl. ............................. 378/16; 378/145; 378/110
[58] Field of Search ................................. 378/4, 16, 15, 378/19, 96, 97, 94, 108, 109, 110, 111, 112, 116, 145, 146

[56] References Cited

U.S. PATENT DOCUMENTS 5,228,070   7/1993   Mattson .................................. 378/19
5,379,333   1/1995   Toth ....................................... 378/16

Primary Examiner—David P. Porta
Assistant Examiner—Don Wong
Attorney, Agent, or Firm—Quarles & Brady

[57] ABSTRACT

An x-ray CT system modulates x-ray tube current as a function of gantry angle to reduce the total patient dose without significantly increasing image noise. A modulation waveform is stored in a table as a function of gantry angle, and during a slice acquisition, values are periodically read from this table and employed to calculate tube current commands. Tube current is monitored and compared with the latest command to ensure the proper x-ray dose is applied.

6 Claims, 5 Drawing Sheets

MODULATION OF X-RAY TUBE CURRENT DURING CT SCANNING

BACKGROUND OF THE INVENTION

The present invention relates to computed tomography (CT) imaging apparatus; and more particularly, to the modulation of x-ray dose applied to a patient during a scan.

In a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

Quantum noise degrades the diagnostic quality of a CT image and this noise is related to the amount of x-rays, or "dose", employed to acquire the attenuation measurements, and to the attenuation characteristics of the patient. Image artifacts due to noise will increase if the x-rays measured at the detector drop to low levels either because the prescribed x-ray dose is too low or the beam is highly attenuated by patient anatomy. The x-ray dose is controlled during the exposure by the emission current ("mA") which flows in the x-ray tube, and the practice in the past has been to fix this current at a level which provides a constant dose during the entire scan. However, more recently the x-ray dose has been varied during the scan by modulating the x-ray tube current from slice-to-slice and during the acquisition of each slice. This method is described for example in co-pending U.S. patent application Ser. No. 155,037 filed on Nov. 19, 1993 and entitled "Variable Dose Application By Modulation of X-Ray Tube Current During CT Scanning" U.S. Pat. No. 5,319,333.

There are a number of practical problems in implementing variable dose through tube current modulation. First, to be effective, the x-ray tube current must be modulated at a rate which is very demanding on the x-ray controller. In addition, safety requires that the x-ray dose be carefully monitored and this is complicated when the dose is continuously modulated throughout the scan.

Summary of the Invention

The present invention relates to a CT imaging system in which the x-ray dose is modulated as the gantry is rotated during a scan. More specifically, the present invention is a CT system which includes gantry angle means for indicating the gantry angle at regular intervals during a scan, a basis table for storing a modulation waveform as a function of gantry angle, means for reading a value from the basis table using the gantry angle, and calculating means for producing a current command for the x-ray ray tube based on the value from the basis table.

A general object of the invention is to produce current commands for an x-ray tube that are modulated in accordance with a known waveform. The waveform is stored as a table and values are read out using a function of gantry angle as an index into the table. The table values may be normalized to make them more generally applicable, in which case a modulation index is used in combination with the table value and a maximum current command to calculate the current command.

In another aspect of the invention the x-ray dose applied to a patient is monitored during the scan by a feedback signal which indicates x-ray tube emission current. The feedback signal is compared to the current command produced during the previous time interval to determine if the x-ray dose is significantly different from the modulated current command.

DETAILED DESCRIPTION OF THE INVENTION

Figure 1:
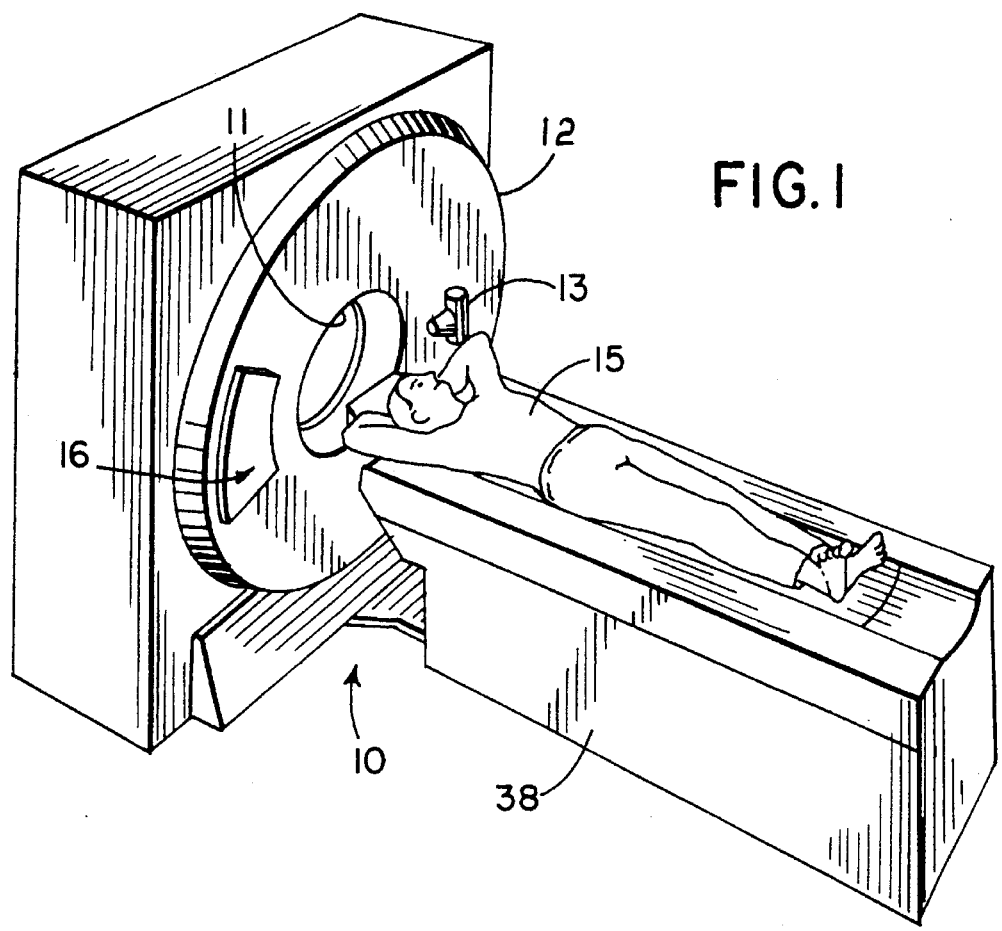
FIG. 1 is a pictorial view of a CT imaging system in which the present invention may be employed.
Figure 2:
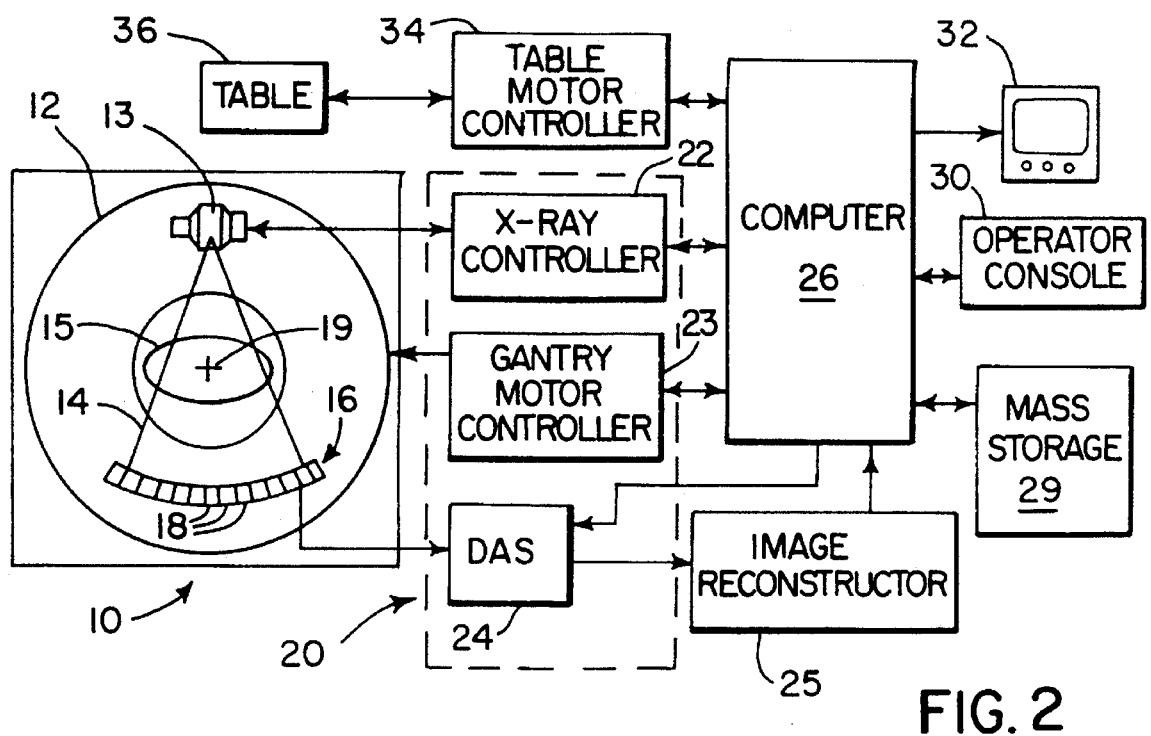
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15. A reference detector at one end of the array 16 measures the unattenuated beam intensity during the scan to detect variations in the applied x-ray dose.

This reference data is used in subsequent processing of the x-ray projection data to normalize it to a common reference dose.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer system 26 which stores the image in a mass storage device 29.

The computer system 26 also receives commands and scanning parameters from an operator via console 30 that has a keyboard. An associated cathode ray tube display 32 allows the operator to observe the reconstructed image and other data from the computer system 26. The operator supplied commands and parameters are used by the computer system 26 to provide control signals and information to the DAS 24, the x-ray controller 22 and the gantry motor controller 23. In addition, computer system 26 operates a table motor controller 34 which controls a motorized table 36 to position the patient 15 in the gantry 12. It can be appreciated by those skilled in the art that the computer system 26 may include multiple processors which are separately programmed and interconnected in a system which performs these functions.

Figure 6:
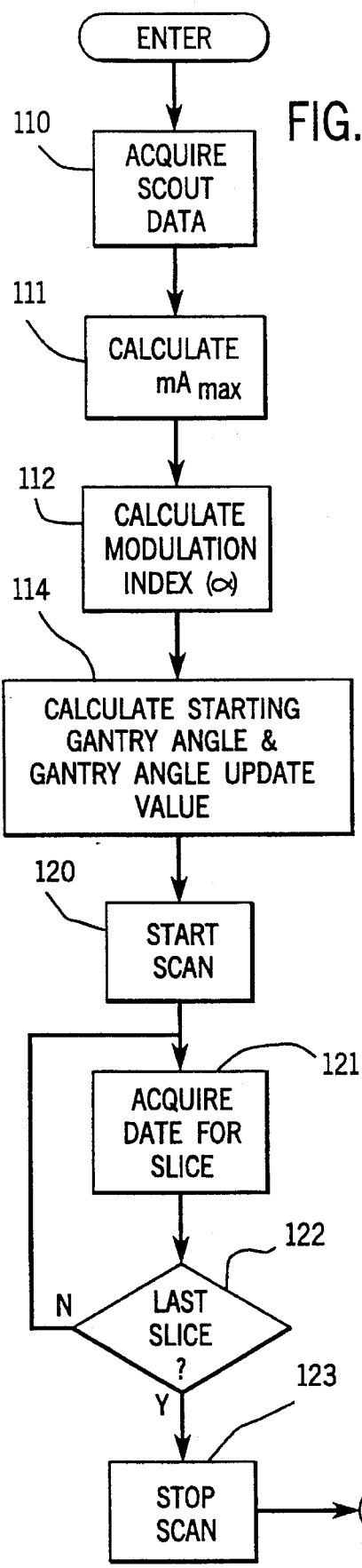
FIG. 6 is a flow chart of a program executed by the computer system of FIG. 5 to conduct a scan.

Referring particularly to FIG. 2, the computer system 26 directs the system components to carry out the prescribed scan in accordance with stored programs. If an mA modulation strategy is selected by the operator, the program illustrated by the flow chart in FIG. 6 is executed by computer system 26 to implement the preferred embodiment of the present invention. The first step is to acquire scout data, as indicated at process block 110. This scout data is comprised of two orthogonal views from each slice in the prescribed scan, and in the preferred embodiment, one is acquired at a gantry angle of 0° and the other at an angle of 90°. The next step, as indicated at process block 111, is to calculate the maximum x-ray tube current ($mA_{max}$) for each slice using the scout data. This is described in copending U.S. patent application Ser. No. 08/155,045 filed on Nov. 19, 1993 and entitled "Dynamic Dose Control In Multi-Slice CT Scan", which is incorporated herein by reference. This enables the x-ray dose to be reduced for slices with reduced attenuation of the x-ray beam without exceeding the prescribed image noise. It results in an array of stored values ($mA_{max}$), one for each of the respective slices in the scan.

Similarly, as indicated at process block 112, a set of modulation indexes are also calculated from the scout data. This is described in co-pending U.S. patent application Ser. No. 155,037, filed on Nov. 19, 1993 and entitled "Variable Dose Application By Modulation Of X-Ray Tube Current During CT Scanning", which is incorporated herein by reference. The modulation index is determined from the ratio of the scout data and it indicates the degree to which the x-ray tube current can be modulated during acquisition of a slice without significantly increasing noise artifacts. It results in an array of stored values ($\alpha$), one for each of the slices in the scan.

Prior to starting the scan two values are calculated at process block 114 from scan parameters provided by the operator. The first is the gantry angle at which data will first be acquired for the first slice, and the second value is a number which reflects the rate at which the gantry rotates during the scan. The operator can select rates of 1, 2, 3 and 4 seconds. The selected rate is converted to a "skip value" which represents the change in the basis waveform table index required to synthesize the desired waveform at the appropriate update rate.

$$\text{Skip Value} = \frac{2 * (\text{The number of basis waveform table entries for one complete waveform})}{[\text{Gantry Rate}/(\text{the update rate})]} \quad (1)$$

Although many combinations are possible, a basis waveform table with half degree step resolution, traversed at a 25 msec update rate has been shown to be satisfactory.

Referring still to FIGS. 2 and 6, the computer 26 starts the scan at process block 120, by signaling the gantry motor controller 23. It then enters a loop in which each slice is acquired as indicated at process block 121, until the last slice is detected at decision block 122. The scan is stopped at 123 and the program ends. As will be described in more detail below, each slice is acquired at an appropriate x-ray dose level ($mA_{max}$) and the x-ray dose is modulated during each slice acquisition by an appropriate amount ($\alpha$).

The acquired x-ray profile data is processed in the usual fashion to reconstruct a slice image. Even though the views are acquired with varying x-ray beam intensity, the data is normalized with the reference detector signal as mentioned above so that the reconstruction of the image is performed with x-ray profile data that is essentially equivalent to that acquired with a constant x-ray beam intensity during the entire scan.

Figure 3:
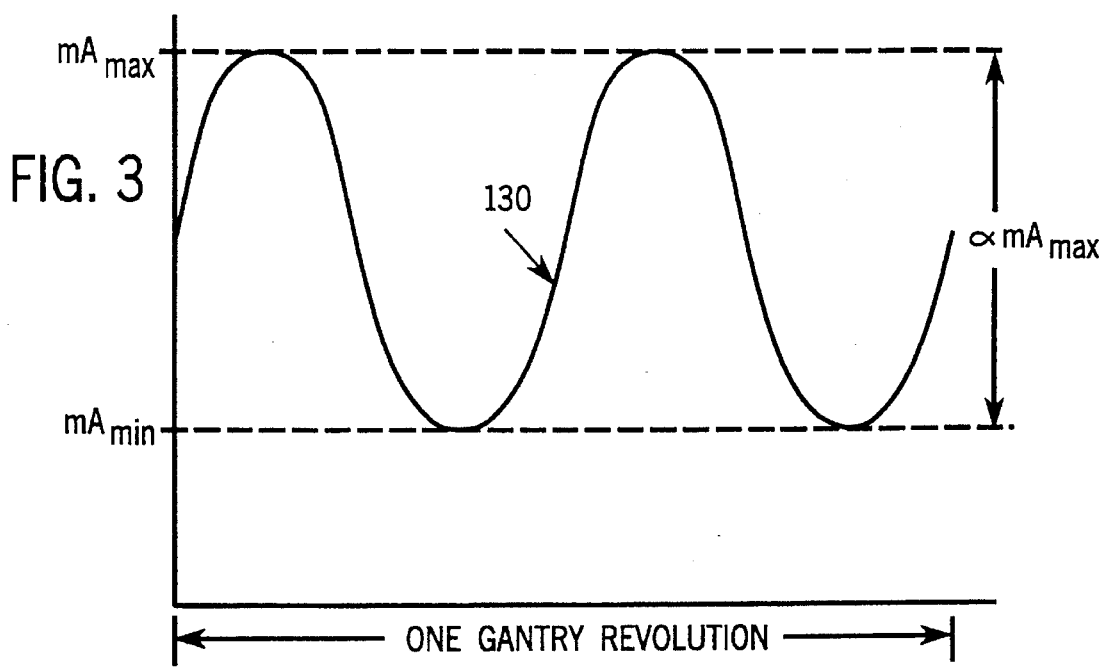
FIG. 3 is a graphic representation of a current modulation profile during one revolution of the CT system gantry.

Referring particularly to FIG. 3, the x-ray tube current command (mA) is modulated during each slice acquisition as a function of gantry angle. During one complete gantry rotation the tube current (mA) is modulated at a frequency twice that of the gantry rotation as indicated by curve 130. The tube current (mA) is modulated from the precalculated maximum dose ($mA_{max}$) to a minimum dose ($mA_{min}$) which is determined by the precalculated modulation index ($\alpha$). It is an objective of the present invention to accurately output x-ray tube current commands (mA) which follow the curve 130. It is also an objective of the present invention to monitor x-ray tube current during the slice acquisition to insure that the proper dose is being applied to the patient.

Figure 5:
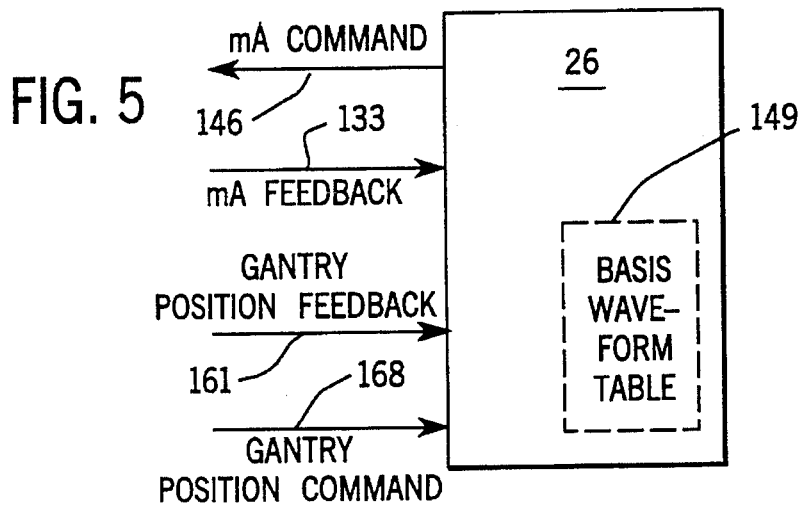
FIG. 5 is a block diagram of the computer system which forms part of the CT system of FIG. 2.
Figure 8:
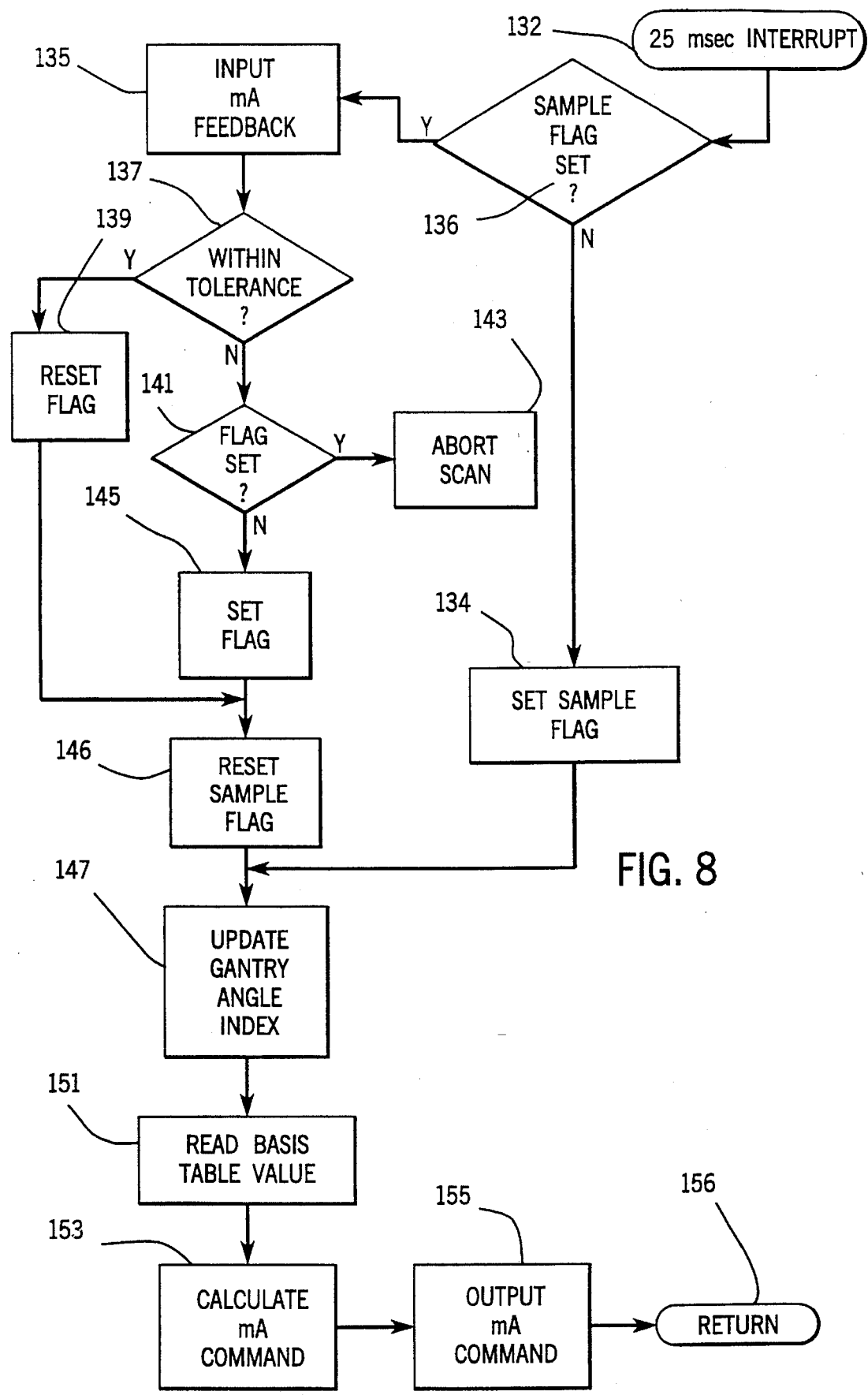
FIG. 8 is a flow chart of a program executed by the computer system of FIG. 5 to control x-ray tube current.
Figure 9:
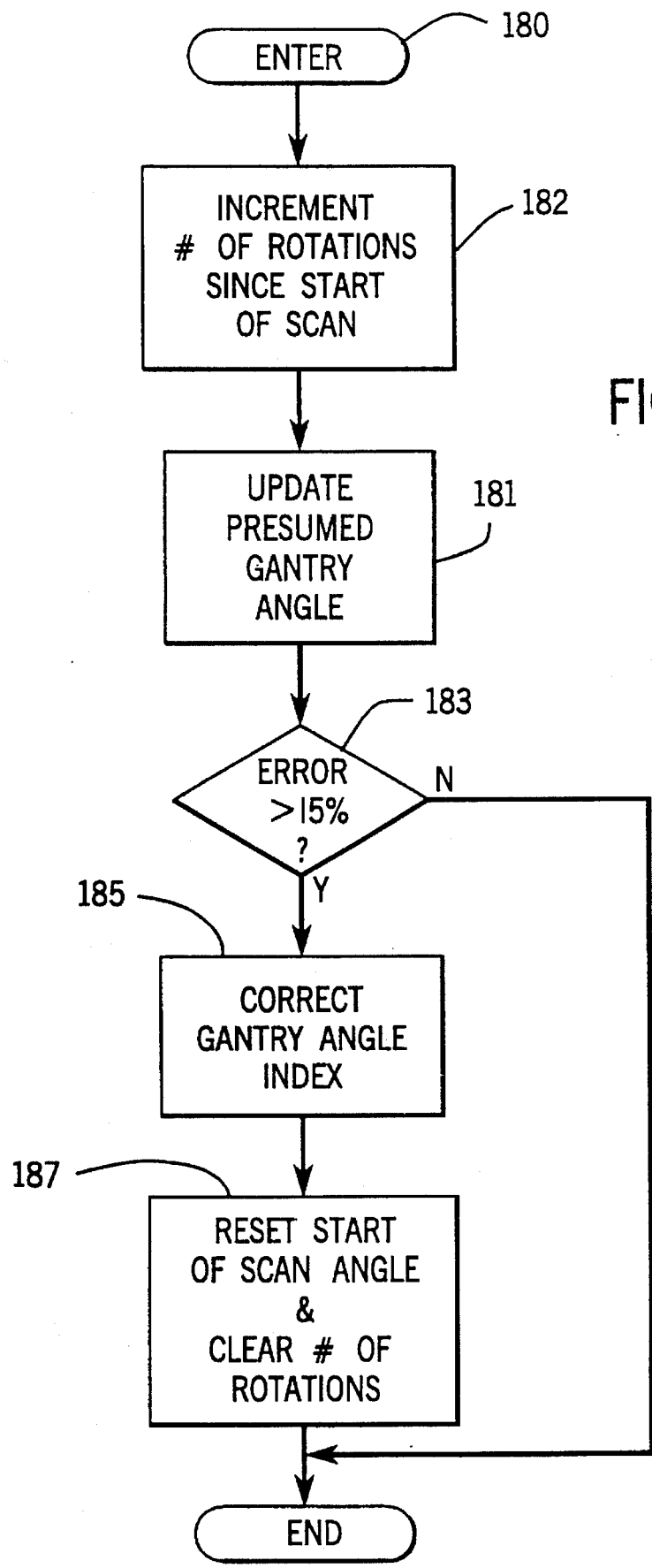
FIG. 9 is a flow chart of another program executed by the computer of FIG. 5 to correct the gantry angle index employed in the program of FIG. 8.

Referring particularly to FIGS. 5 and 8, the computer 26 performs these functions under the direction of an interrupt routine that is executed repeatedly during each slice acquisition. In the preferred embodiment this routine is entered every 25 msecs at 132 and a "sample" flag is checked at decision block 136 to determine if an mA feedback signal 133 from the x-ray controller 22 is to be input at process block 135. This mA feedback signal is compared with an mA command signal produced during the previous 50 msec sample interval, and if the two values are within a preselected tolerance (for example, 3% to 10%) of each other, the process branches at decision block 137 to reset a flag at process block 139. If the mA feedback signal is not within tolerance, the same flag is tested at decision block 141 to determine if it was set during the previous 50 millisecond interval. If so, the scan is aborted as indicated at process block 143, and if not, the flag is set at process block 145. As a result, the continuously changing x-ray tube current is continuously monitored to ensure that it is following the commanded waveform. If the tube current is out of tolerance for two consecutive 50 millisecond intervals, a malfunction is presumed and the scan is aborted.

The sample flag is reset at process block 146 so that during the next 25 msec interrupt this monitoring function is skipped. The sample flag is set a process block 134 during the next interrupt.

After the monitoring function is completed a new tube current command (mA) 146 is calculated. As indicated in FIG. 8 at process block 147 this is done by first updating a gantry angle index to reflect the amount of gantry motion during the previous time interval. This update amount is the skip value calculated prior to the start of data acquisition and described above in equation (1).

Figure 4:
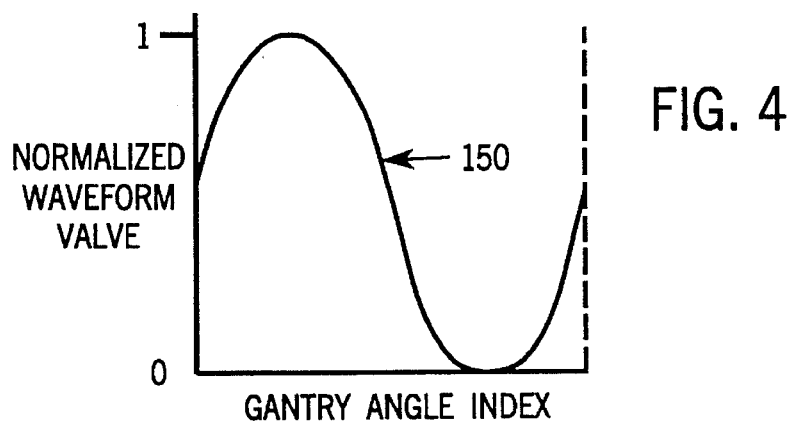
FIG. 4 is a graphic representation of a normalized waveform used by the present invention to produce the current modulation profile of FIG. 3.

As shown in FIG. 5, a basis waveform table 149 is stored in the computer 26. As indicated by curve 150 in FIG. 4, this table 149 indicates the normalized value of the modulation waveform in increments (for example, 0.25° or 0.5°) over a 180° range of gantry rotation. The updated gantry angle index is used to read a value from the table 149 as indicated at process block 151, and then calculate an mA command for the current update interval as indicated at process block 153. Since the basis waveform table 149 only stores the modulation waveform for 180 degrees of gantry angle, when the gantry angle index exceeds 180°, it is recycled through the table by subtracting 180° before using it to read from the table 149. It can be appreciated by those skilled in the art that the normalized waveform 150 is substantially sinusoidal in the preferred embodiment, but other shapes are possible depending on the particular anatomy being imaged.

The mA command is calculated at process block 153 using the following equation:

$$\text{mA command} = \text{mA}_{max}(1-(\alpha * \text{basis table value})) \quad (2)$$

This calculation can be done quickly in "real time" and the resulting mA command is immediately output to the x-ray controller 22 as indicated at process block 155. The system then returns from the interrupt at 156 to perform other functions as will now be described.

Figure 7:
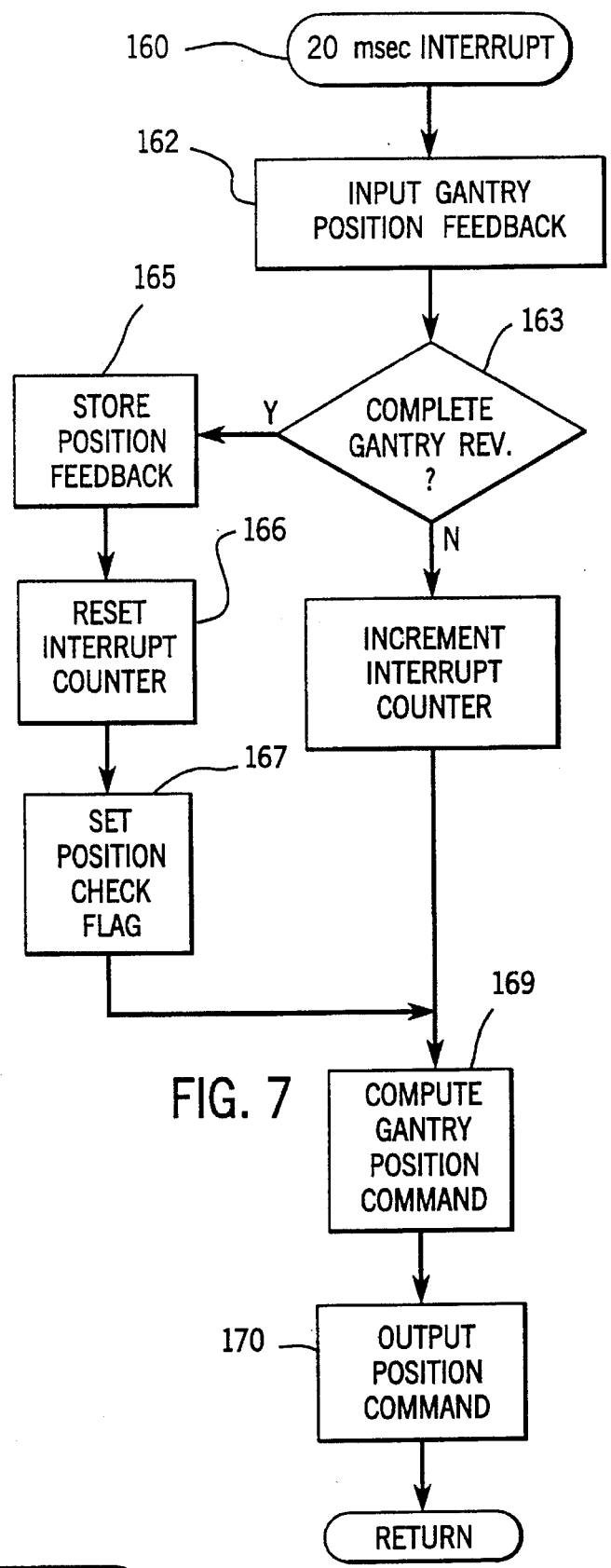
FIG. 7 is a flow chart of another program executed by the computer system of FIG. 5 to control gantry position.

Referring particularly to FIGS. 5 and 7, the computer 26 executes a 20 msec interrupt routine which controls gantry rotation through the gantry motor controller 23. Every 20 milliseconds the program is entered at 160 and a gantry position feedback signal 161 is input at process block 162. This signal is the accumulated counts from an incremental shaft encoder (not shown) that measures gantry rotation since it was last reset to zero during a reference operation which occurs between scans. At the start of the scan, the gantry feedback position is stored as the "start of scan gantry position". By using the known gantry period and the number of 20 msec interrupts for one revolution a complete gantry revolution can be detected by counting the interrupts. This event is detected at decision block 163, and when it occurs, the position feedback signal is stored as indicated at process block 165, and the 20 msec interrupt counter is reset at process block 166. A position check flag is set at process block 167 to activate a task described below which ensures that the gantry angle index described above closely follows the true gantry angle indicted by the gantry feedback signal 161. A new gantry position command 168 is then calculated at process block 169 and output to the gantry motor controller 23 at process block 170. As is well known in the art, the gantry position command is calculated using the gantry position feedback signal 161 and the commanded gantry rotation speed selected by the operator to maintain the gantry rotation at a constant rate during the scan.

As indicated above, the position check flag set by the 20 msec interrupt routine activates a task which checks for proper gantry angle indication. This task is entered at 180 and the presumed gantry angle is updated at process block 181 and the number of rotations completed since the start of scan is incremented at process block 182. The presumed gantry angle is computed at process block 181 using the formula:

$$\text{presumed gantry angle} = \text{start of scan gantry position} + \quad (3)$$

$$((\text{number of encoder counts per rotation}) *$$

$$(\text{number of rotations completed since the start of scan}))$$

The present gantry position is compared with the presumed gantry position for the completed rotation as indicated at decision block 183. If the present gantry position deviates from the expected value by more than 15 degrees, then the gantry angle correction is computed at process block 185 and sent to the 25 msec interrupt handler to be used to correct the indexing on the next 25 msec interrupt. The start of scan gantry angle is then reset at process block 187 to the present gantry angle, and the number of rotations completed since start of scan is cleared. If the present gantry position does not deviate more than 15 degrees, then no correction is sent to the 25 msec interrupt handler. The gantry angle correction is the number of 0.25 degree counts necessary to bring the gantry angle index into alignment with the gantry position feedback signal, and it will have an affect when the next 25 millisecond interrupt occurs to calculate a new mA command.

It should be apparent to those skilled in the art that many modifications can be made to the preferred embodiment described herein without departing from the spirit of the invention. For example, other preset modulation profiles may be stored and presented to the operator for use during the scan. Also, while the sinusoidal shape at twice the gantry frequency is preferred as the general purpose template, other shapes are possible. Also, while the patient projection data is obtained in a scout scan in which views are acquired at gantry angles of 0° and 90° in the preferred embodiment, different angles can be used and more scout views can be acquired to gather the patient attenuation profile information. Also, the patient projection data may be acquired in a helical survey scan or from an adjacent slice which has already been acquired. It should also be apparent that the present invention is applicable to a CT system which acquires each slice either while the patient table is stationary or in a spiral scan in which the table is moved continuously throughout the data acquisition.

We claim:

1. A method for modulating the dose of an x-ray beam applied to a patient by an x-ray CT system during a scan, the steps comprising:

calculating a command $\text{mA}_{max}$ which determines the maximum dose of the x-ray beam;

storing a waveform table indicative of the desired modulation as a function of an x-ray CT system gantry angle;

periodically during the scan calculating an mA command which controls the dose of the x-ray beam by:
  a) determining the current x-ray CT system gantry angle;
  b) reading a value from the stored waveform using the x-ray CT system gantry angle as an index into the waveform table; and
  c) multiplying the command $\text{mA}_{max}$ by the value read from the waveform table; and outputting the calculated mA command to an x-ray controller which controls the dose of the x-ray beam.

2. The method as recited in claim 1 which includes:

periodically during the scan monitoring the dose of the x-ray beam applied to the patient by: inputting an mA feedback signal indicative of the x-ray beam dose;

comparing the mA feedback signal with the last mA command output to the x-ray controller; and producing an out-of-tolerance condition if the mA feedback signal differs from the last mA command by more than a preselected amount.

3. The method as recited in claim 2 in which the out-of-tolerance condition stops the scan of the patient.

4. The method as recited in claim 2 in which the mA command determines current in an x-ray tube which produces the x-ray beam, and the mA feedback signal indicates the amount of current in the x-ray tube.

5. The method as recited in claim 2 which includes the step of calculating a modulation index ($\alpha$) and step c) is carried out by performing the following calculation:

$$\text{mA command} = \text{mA}_{max}(1 - (\alpha * \text{ waveform table value})).$$

6. The method as recited in claim 1 in which the current x-ray CT system gantry angle is determined by periodically inputting a gantry position feedback signal.

* * * * *